Figure 1:
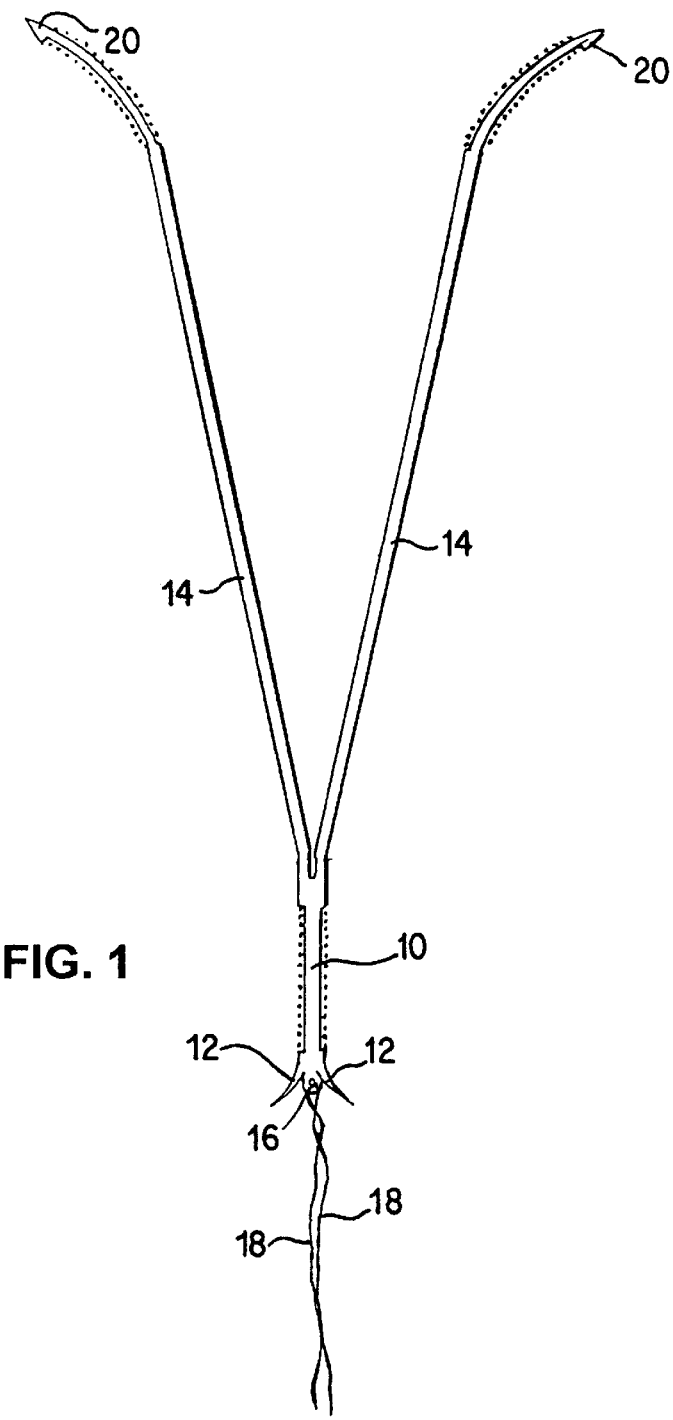

United States Patent
Turin

[11] Patent Number: 6,119,696
[45] Date of Patent: Sep. 19, 2000

[54] INTRAUTERINE DEVICE FOR USE AS A CONTRACEPTIVE MEANS IN FEMALE DOGS AND METHODS OF INSERTION THEREOF

[76] Inventor: Enrique Horacio Turin, Vergara Campo 150, Pergamino, 2700 Province of Buenos Aires, Argentina

[21] Appl. No.: 08/834,424

[22] Filed: Apr. 16, 1997

[30] Foreign Application Priority Data

Apr. 22, 1996 [AR] Argentina ............................ 960102277

[51] Int. Cl.[7] ...................................................... A61F 6/06
[52] U.S. Cl. ......................... 128/830; 128/833; 128/839; 128/840
[58] Field of Search ..................................... 128/830–841

[56] References Cited

U.S. PATENT DOCUMENTS

| | | |
|---|---|---|
| 3,913,572 | 10/1975 | Wheeler ................................. 128/833 |
| 3,913,573 | 10/1975 | Gutnick ................................. 128/833 |
| 4,111,196 | 9/1978 | Emmett ................................. 128/833 |
| 4,117,838 | 10/1978 | Hasson ................................... 128/833 |
| 4,353,363 | 10/1982 | Sopena Quesada .................... 128/833 |
| 4,578,076 | 3/1986 | Luukkainen ........................... 128/833 |
| 4,932,421 | 6/1990 | Kaali ..................................... 128/833 |
| 5,146,931 | 9/1992 | Kurz ...................................... 128/833 |
| 5,417,223 | 5/1995 | Aarnio .................................. 128/833 |

*Primary Examiner*—Michael A. Brown
*Attorney, Agent, or Firm*—Evenson, McKeown, Edwards & Lenahan, P.L.L.C

[57] ABSTRACT

An intrauterine device to be used as a contraceptive means designed for insertion into female dogs, that comprises a body and four diverging branches, two of which emerge from the bottom end of the body and the other two exit from the top end of the body substantially in the shape of a V, with both of the branches in the top end having a length that is 4–5 times greater than the length of the body and with each branch of the top end terminating in the shape of a half wedge; the device further having a copper filament wound on the body, and on each of the top end branches, and also having an eyelet in the bottom end of the body for the nylon thread. A method for insertion of said intrauterine device is also provided.

3 Claims, 1 Drawing Sheet

INTRAUTERINE DEVICE FOR USE AS A CONTRACEPTIVE MEANS IN FEMALE DOGS AND METHODS OF INSERTION THEREOF

The present invention relates to an intrauterine device and a drug-free reversible method designed to prevent conception in female dogs.

The instant method consists of inserting a device that is adapted to the anatomy of the uterine cavity, and it avoids conception just by its mere presence, without producing any side effects or altering sexual behavior.

Intrauterine devices (IUDs) are the most efficient method of birth control in humans (World Health Organization, 1987). Its mechanism of action, by which fertility is suppressed in humans, has been an object of controversy, due to the diversity of mechanisms of action found in assays carried out in various animal species (Marston and Kelly, 1966).

In women and non human primates, the IUD interferes with fertilization without altering de menstrual cycle. (Chi, 1993).

In rodents, the IUD does not affect ovulation, passage of sperm, or fertilization, but it does interfere with implantation through three mechanisms:

a) embryo degeneration;

b) acceleration of embryo's passage and expulsion and c) alteration of the uterine component of implantation or deciduoma (Marston and Kelly, 1966).

In rodents with two uterine cornua and two separate cervices, such as rats and rabbits, the anti-implantation effects are achieved when an IUD is placed in each cornu (Davis, 1972). In mice, wherein both projections are joined by a common cervix, the insertion of an IUD is enough to prevent the embryo's implantation in both cornua (Marston and Kelly, 1966).

In rodents and ruminants, which have two independent uterine cornua,, contraceptive effects are achieved when an IUD is inserted in each cornu (Marston and Kelly, 1966, Davis 1972, Hawk et al, 1973).

In ruminants, such as sheep and cows, apart from the contraceptive effect, the alteration of the estral cycle may take place depending on the degree of relaxation the IUD causes in the uterus (Nalbandov et al, 1955; Hansel and Wagner, 1960; Turin et al, 1996).

In ovines, the insertion of an IUD interferes with the estral cycle without inhibiting ovulation. In these animals, the contraceptive effect seems to respond to an alteration in the passage of sperm and early luteolysis. This phenomenon might be caused by the relaxation of the uterus after insertion of the IUD and it shows on insertion of the IUD in an homolateral position with respect to the ovulating ovary. (Anderson et al, 1969).

The art literature suggests that insertion of an IUD in bovines does not change the intensity of the estrus, although it exerts a contraceptive effect through the variation of the passage of sperm and promotion of an early luteolysis by the relaxation of the uterus. The size and location of the IUD appear to be determining factors in its contraceptive performance (Marston and Kelly, 1966; Hawk et al, 1968).

At present there are no reports in the prior art on the effects of IUDs in female dogs. Apparently, the difficult access to the uterine cavity via the vagina in these animals has been one of the impediments to further these studies. In bitches, neutering and hormonal therapy are the most commonly used means to control their reproduction (Burke, 1986). Neutering involves high costs, surgical risk, side effects and irreversibility, whereas hormonal methods produce undesirable side effects.

After the research that led to the development of IUDs for human use was finished, experimenting of such devices on animals was dropped and this methodology was not believed to be applicable to many of the animal models on which this development was effected.

In a survey carried out in the United States on the subject of birth control methods, which are in use at present in various species of primates and carnivorous animals, it is shown that hormonal implants and neutering are the most widely used contraceptive means. The survey does not mention the IUD as a contraceptive means in animals (Porton and Baker, 1990).

According to known prior art background, heretofore an IUD has never been used as a common contraceptive method in house animals. The existing data on this subject, related to the above mentioned species, come from assays on prototypes for human use or from research on the mechanism of action of IUDs for its extrapolation to the human being.

The object of the intrauterine device and the method of this invention is preventing fertilization and/or nesting in the canine uterus. While the contraceptive action of IUDs occurs with or without alterations of the estral cycle, it is a generally accepted fact that the mechanism by which it interferes with fertility relies merely on:

1—Gametocidal action of copper on sperm, ovules and, eventually, embryos through ion release (Corfam and Segal, 1968).

2—Irritation by local mechanical action which inhibits the endometrial component of implantation.

The intrauterine device of this invention, designed for insertion into female dogs, comprises a body and four diverging branches, two of which protrude from the bottom end of the body and the other two emerge from the top end of the body substantially in the shape of a V, with both of the top end branches having a length that is 4–5 times greater than the length of the body and with each of said top end branches terminating in a half wedge; the device further having a copper filament wound on the body, and on each of the top end branches, and also having an eyelet in the bottom end of the body for the nylon thread.

The studies that have been performed on a significant number of female dogs of different breeds, with exemplary IUDs designed especially for that purpose in accordance with the present invention, have shown the feasibility of application of the instant method to interfere with reproduction without altering the animal's estral cycle or sexual behavior. The contraceptive mechanism of action in the bitch relies on the gamototoxic action of copper and the local irritation the IUD causes at the endometrial level, thus inhibiting implantation. The main advantage offered by the device provided by this invention is that it allows reproduction to be controlled in a reversible way, without resorting to neutering or hormonal therapy, thus becoming a more economic, effective and desirable tool to fight undue reproduction of the dog population and the consequent risk to public health.

In order to disclose the advantages of the device of the present invention, to which users and persons of ordinary skill in the art will of course be able to add many more, and in order to make the understanding of its constitutive features easier, there is provided below an embodiment by way of example. Said example is schematically shown, without any specific scale in the annexed drawing, with the express proviso that this drawing should not be construed as limitative or exclusive of the scope of this invention.

The device in accordance with this invention is made of low density polyethylene and it consists of (see FIG. 1) a body (10), and four diverging branches, two of which (12) emerge from the bottom end of the body, being its 90° angle oriented toward said end; and the other two branches (14) come from the top end of the body and their 30° angle opens upward in substantially a V shape, emulating the analogous anatomy of the uterine cornua. The dimensions of the body and branches vary depending on the size of the receiving uterus. An example of a device of the present invention could consist of a device comprising a body length of between 15 and 25 mm, whereas the length of the top branches 14 varies between 50 and 100 mm and the bottom branches 12 are about 10 mm long. The diameter of about 2 mm is consistent throughout de IUD (folded branches). Each of the top end branches has a 1 mm diameter. The IUD is covered by a copper filament wound on three regions of the device:

1. on the body 10, taking two fourths of the central region.
2. on each of the top branches 14, taking the top fifth of the same.

The bottom end of the body has an eyelet 16 for the 20 centimeter long nylon thread 18 which is provided for removal of the device from the uterine body. Each distal end of the top branches provides a thickening in the shape of a half wedge 20 which, when the branches are folded, become a wedge that has a base diameter of 2.5 mm and a sharp top end. The purpose of this wedge 20 is dilating the cervical canal and guiding the IUD through said cervical canal into the cavity of the uterine body, during insertion of the IUD into the uterus.

The device comprises a structure that differs from the existing counterparts for insertion into human beings and is also different from the device developed to inhibit estrus in bovines (Turin et al, 1996). The canine IUD is fully adapted to the anatomy of the uterus, which comprises a small body 10 which extends into two cornua 10 in the shape of a V, each of which has a length that is 4–5 times greater than the body. The cornua 14 support the embryo's implantation and the fetal load during pregnancy. This structure avoids the need to place an IUD for every cornu, as is necessary in cows.

The following table summarizes the similarities and differences between a canine IUD and other devices designed for humans and bovines:

|  | Canine IUD | Bovine IUD | Human IUD |
|---|---|---|---|
| Material | Low density polyethylene | Low density polyethylene | Low density polyethylene |
| Copper area (Cu) | 600–800 mm$^2$ | 300 mm$^2$ | 200–380 mm$^2$ |
| Cu Location | body and branches | body | body or branches |
| In situ configuration |  |  |  |
| Folded length | 65–125 mm | 50–70 mm | 40–40 mm |
| Diameter (approx.) | 2 mm | 2,5–3 mm | 2,2–2,5 mm |
| Branches | 4 | 2 | 1–2 |
| Sterilization | yes | no | yes |
| Number of uteri | 1 | 2 | 1 |

Figure 2:
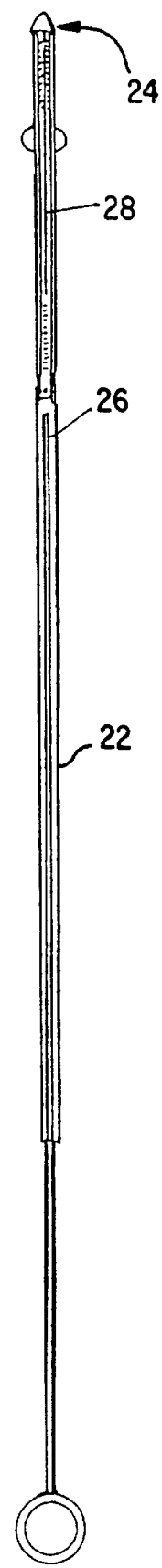

The intrauterine device of the present invention is inserted by means of an introducer designed for that purpose (see FIG. 2). This introducer has a tube 22 made of acetal resin, with dimensions varying between 10 to 20 centimeter in length, an outer diameter of 3 mm and an inner diameter of 2.3 mm. The tube is provided with an outer enlargement placed at a variable distance (30–40 mm) from the insertion end 24, which determines the depth of insertion of the tube into the cervical canal. Inside the tube there is a slidable piston 26 which ejects the device 28 from the tube 22 after said device has been introduced into de body of the uterus. It also has two polypropylene protrusions especially designed to facilitate handling of the device.

The insertion procedure of said device comprises the steps of:

1—Sedating the animal;
2—Placing the animal on a table, on its back, with its hind quarters raised;
3—Cleaning the vulvar region and vaginal entrance with an antiseptic solution;
4—Pulling the cervix toward the vulvar labia by nipping the roof of the vaginal vestibule;
5—Inserting the tube of the introducer, with the IUD inside, and with the IUD's wedged end protruding to dilate the cervix, into the cervical opening, up to the center region of the uterine body. The length is determined by the top of the introducer tube;
6—Expelling the IUD into the body of the uterus by exerting pressure on the piston. The branches unfold as the IUD is expelled from the tube. Each of the top branches is directed toward the appropriate cornu whereas the bottom branches attach the body of the IUD to the uterine body;
7—The introducer tube is withdrawn and the nipped uterus is released;

In case of difficulties in insertion the use of an especially designed endoscope is contemplated, which allows for observation of the cervical opening in female dogs of different sizes. This endoscope is provided with a battery holder handle and a miniature light bulb in its opposite end provided for lighting the interior of the vaginal vestibule. It is provided in three different tube sizes adaptable to different vaginal vestibules.

The accurate insertion of the IUD can be validated by echography.

REFERENCES

Burke, T. J. (1986): Population in the bitch. En: Current Therapy in Theriogenology. Editor: Morrow D. A. W. B. Saunders Co. Fiadelfia USA página 528

Corfman. P. A., Segal, S. J. (1968). Biologic effects of intrauterine devices. Am. J. Obstet. Gynecol. 100:448.

Davis, H. J. (1972). Intrauterine contraceptive devices. Present status and future prospects. Arn. J. Obstet. Gynecol. 114:134.

Hansel, W.; Wagner, W. C. (1960). Luteal inhibition in the bovine as a result of oxytoxin injections, uterine dilatation and intrauterine infusions of seminal and preputial fluids. J. Dairy Sci. 43:786.

Hawk, H. W.; Conley, B. S.; Brinsfield, T. H.; Righter, B. (1973). Contraceptive effect of plastic devices in cattle uteri. En: Intrauterine Contraception. Editor: S. J. Segal; A. L. Southam y D. K. Shafer. University of Wisconsin Press. p. 189.

Marston, J. H.; Kelly, W. A. (1966). The effects and mode of action of intra-uterine devices. Vet. Rec. 79:644.

Nalbandov, A. V.; Moore, H. W. (1955). Further studies on the neurogenic control of estrus cycle by uterine distention. Endocrinology 56:225.

Porton, I.; Baker, A. (1990). Survey results on the use of birth control methods in primates and carnivores in North American Zoos. AAZPA Annual Conference Proceedings p. 489.

Turin, E.; Nagle, N. A.; Lahoz, M.; Turin, M.; Escofet, M. B.; Mendizabal, A.; Torres, M. (1 996). Anestrus induced by a cooper-bearing intrauterine device in heifers. Effects on body weight gain and on progesterone and testosterone levels. Sent to Theriogenology.

World Health Organization (1987). Mechanism of action, safety and efficacy of intrauterine devices. W. H. O. Technical Report. Series 753, p, 91

I claim:

1. An intrauterine device to be used as a contraceptive means designed for insertion into female dogs, characterized by comprising a body and four diverging branches, two of which emerge from the bottom end of the body and the other two exit from the top end of the body substantially in the shape of a V, with both of the branches in the top end having a length that is 4–5 times greater than the length of the body and with each branch of the top end terminating in the shape of a half wedge; the device further having a copper filament wound on the body, and on each of the top end branches, and also having an eyelet in the bottom end of the body for the nylon thread.

2. A method of insertion of said intrauterine device in female dogs, characterized by comprising the introduction of the intrauterine device according to claim 1 into the uterus of a female dog by means of an introducer, wherein the top end branches of the device are folded in the insertion end of said introducer, with both of their wedges protruding from it.

3. The method of claim 2 designed to prevent conception, characterized by comprising the insertion of the intrauterine device such that the extremities are inserted into the uterine cornua to prevent fertilization ad/or nesting in the canine uterus.

* * * * *